United States Patent [19]

Grandadam et al.

[11] 4,192,870
[45] Mar. 11, 1980

[54] NOVEL ZOOTECHNICAL COMPOSITIONS

[75] Inventors: Jean A. Grandadam, Saint-Maur des Fosses; Alain Jobard, Le Blanc-Mesnil; Jean-Pierre Scheid, Bondy, all of France

[73] Assignee: Roussel Uclaf, Paris, France

[21] Appl. No.: 898,872

[22] Filed: Apr. 21, 1978

[30] Foreign Application Priority Data

Apr. 27, 1977 [FR] France ................. 77 12731

[51] Int. Cl.$^2$ ............................ A61K 31/56
[52] U.S. Cl. ............................ 424/240
[58] Field of Search ..................... 424/240

[56] References Cited

U.S. PATENT DOCUMENTS 3,036,917  5/1962  Harrop ..................... 424/240
3,989,828  11/1976  Aries ....................... 424/240

OTHER PUBLICATIONS

Chem. Abstracts vol. 80 (1974) Pars. 69,649 (m) and 141,366 (N.)

Primary Examiner—Elbert L. Roberts

Attorney, Agent, or Firm—Hammond & Littell, Weissenberger and Muserlian

[57] ABSTRACT

Novel zootechnical compositions and a method of upgrading domestic animals such as cattle by administering under the skin of said animals a mixture of zeranol and an anabolisant steroid of the formula

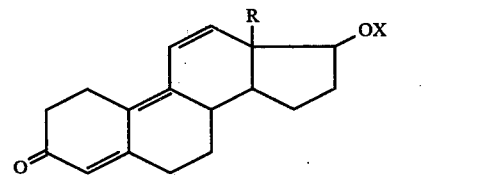

wherein R is alkyl of 1 to 3 carbon atoms and X is selected from the group consisting of hydrogen, lower alkyl of 1 to 6 carbon atoms, lower alkenyl and lower alkynyl of 2 to 6 carbon atoms in which one of the carbon atoms may be replaced with an oxygen atom and acyl of an organic carboxylic acid of 1 to 18 carbon atoms.

18 Claims, No Drawings

NOVEL ZOOTECHNICAL COMPOSITIONS

STATE OF THE ART

German Pat. No. 1,047,596 describes cattle feed containing an estrogenic compound and testosterone or a testosterone derivative (essentially androgenic products) but there is no suggestion therein of using an anabolisant agent. Canadian Pat. No. 889,253 describes compositions for the breeding of pigs based on methyltestosterone and diethylstilbestrol which are susceptible of leaving hormonal substances in organs of the animals notably diethylstilbestrol whose digestive metabolism is complex and whose elimination is slow. For this reason, there is a fear that the active principles with a hormonal action can be found in the slaughtered animals which can be absorbed by the consumer.

U.S. Pat. Nos. 3,939,265 and 3,919,420 as well as French Pat. Nos. 2,271,832, 2,238,476 and 2,250,518 describe other types of zootechnical compositions.

OBJECTS OF THE INVENTION

It is an object of the invention to provide novel zootechnical compositions for increasing the weight of breeding animals.

It is another object of the invention to provide a novel method of increasing the weight and upgrading the meat of farm animals such as pigs and cows.

It is another object of the invention to provide a novel method of increasing the general organic resistance of farm animals.

These and other objects and advantages of the invention will become obvious from the following detailed description.

THE INVENTION

The novel compositions of the invention are comprised of mixture of zeranol and an anabolisant steroid of the formula

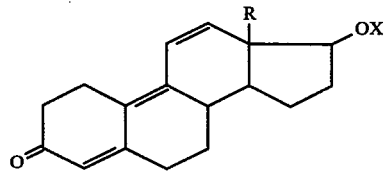

I wherein R is alkyl of 1 to 3 carbon atoms and X is selected from the group consisting of hydrogen, lower alkyl of 1 to 6 carbon atoms, lower alkenyl and lower alkynyl of 2 to 6 carbon atoms in which one of the carbon atoms may be replaced with an oxygen atom and acyl of an organic carboxylic acid of 1 to 18 carbon atoms.

Examples of X substituents are alkyl such as methyl, ethyl, propyl, isopropyl, butyl and isobutyl; alkenyl such as 3-methyl-2-butenyl and 2-methyl-allyl; and alkyl and alkenyl interrupted by an oxygen atom such as methylmethoxy. Examples of suitable carboxylic acids for the acyl group are alkanoic acids such as formic acid, acetic acid, propionic acid, butyric acid, isobutyric acid, undecylic acid; cycloalkylcarboxylic acids such as cyclopropyl carboxylic acid, cyclobutyl carboxylic acid, cyclopentyl carboxylic acid, cyclohexyl carboxylic acid; cycloalkylalkanoic acids such as cyclopropylacetic acid; cyclobutylacetic acid, cyclopentylacetic acid, cyclohexylacetic acid, cyclopropylpropionic acid, cyclopentylpropionic acid, cyclohexylpropionic acid, benzoic acid; and phenylalkanoic acids such as phenylacetic acid or phenylpropionic acid.

Zeranol is described in U.S. Pat. No. 3,239,345 as an anabolic agent and has the formula

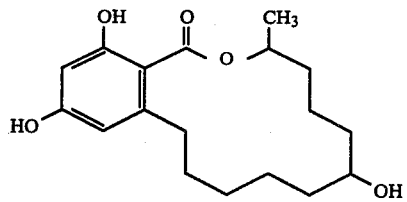

The steroids of formula I are known and are described in French Pat. Nos. 1,380,414 and 1,492,985 as well as Belgium Pat. No. 696,084.

Among the preferred zootechnical compositions of the invention are those wherein R is methyl and those wherein X is acyl of an organic carboxylic acid of 1 to 18 carbon atoms. Particularly preferred are the compositions wherein the compound of formula I is 17$\beta$-acetoxy-$\Delta^{4,9,11}$-estratriene-3-one.

The compositions of the invention promote an increase in the weight of animals such as bovines and pigs. The simultaneous presence of the two active principle reenforce the favorable action against the increase of one and the other so that the result is a sensible greater weight gain.

For bovines, and particularly calves, the compositions may contain 10 to 100 mg, preferably 20 to 60 mg, of zeranol and 50 to 400 mg, preferably 100 to 300 mg of a compound of formula I. When the compositions are to be administered to livestock, the compositions are preferably administered in the form of an implant under the skin, preferably at the base of the ear. The implants can also be deposited in the neck of the animal or in the fessier muscle and may be placed 20 days to 4 months before slaughter. Instead of implants, the compositions can be injected in the form of a suspension or solution. The implants, however, have the advantage that the resorption is slower but more complete.

Among the compounds for increasing the resorption of the compositions in the case of implantation notably, the anti-inflammatory agents can be cited, particularly cortisonic compounds. It is understood that a compound possessing the anti-inflammatory properties of cortisone are characterized by a steroid structure having a 3-keto group, a hydroxy or keto group in the 11-position, a free or esterified ketolic chain in the 17$\beta$-position, a hydrogen or hydroxy in the 17$\alpha$-position and 1 or 2 bonds in the A ring. The rings can also have other substituents such as chlorine or fluorine in the 4-position, methyl, trifluoromethyl or halogen such as fluorine in the 6-position, a halogen such as fluorine in the 9-position, a methyl in the 16$\alpha$ or 16$\beta$-position, or methylene in the 16-position or methylene or difluoromethylene in 6,7-position. The preferred cortisonic steroid is 21-($\beta$-ethoxy-$\beta$-ethoxy-ethoxy)acetate of dexamethasone.

A modification of the invention therefore consists of a composition containing an anabolisant steroid of formula I, zeranol and a cortisonic compound with the preferred compositions being zeranol, a compound of formula I and ($\beta$-ethoxy-$\beta$-ethoxy-ethoxy) acetate of dexamethasone. The composition may contain 0.05 to 5 mg of the cortisonic compound.

The zootechnical compositions of the invention manifest interesting pharmacological properties, namely anabolisant properties, particularly protidic anabolisant properties. These properties mean that the compositions may be used as veterinary medicaments, namely to increase the general organic resistance to aggressions of different types such as to fight against weight loss, emaciation, general organic troubles due to the state of senescence as well as to fight against secondary effects of infections, parasitic and nutritional maladies.

Therefore, the invention is also directed to veterinary medicines containing the said mixture of zeranol and a compound of formula I, especially $17\beta$-acetoxy-$\Delta^{4,9,11}$-estratriene-3-one.

The novel method of increasing the weight of farm animals, particularly pigs and cows, comprising administering to farm animals an effective amount of a composition consisting of a mixture of an anabolisant steroid of formula I and zeranol. The exact amount will depend upon the species of animal.

The novel method for veterinary treatment to increase the general organic resistance of farm animals, comprising administering to farm animals an effective amount of a composition consisting of a mixture of an anabilisant steroid of formula I and zeranol.

In the following examples there are described several preferred embodiments to illustrate the invention. However, it should be understood that the invention is not intended to be limited to the specific embodiments.

EXAMPLE 1

An implant was prepared containing 36 mg of zeranol and 200 mg of $17\beta$-acetoxy-$\Delta^{4,9,11}$-estratriene-3-one (composition A). A second implant was prepared containing 36 mg of zeranol and 140 mg of $17\beta$-acetoxy-$\Delta^{4,9,11}$-estratriene-3-one (composition B). A third implant was prepared from 36 mg of zeranol, 140 mg of $17\beta$-acetoxy-$\Delta^{4,9,11}$-estratriene-3-one and 70$\gamma$ of ($\beta$-ethoxy-$\beta$-ethoxy-ethoxy) acetate of dexamethasone (composition C).

EXAMPLE 2

The influence of zootechnical performances was determined on four groups of male Pie red calves divided into 4 groups. The first group served as the controls, the second group received an implant of composition A from Example 1, the third group received an implant of 36 mg of zeranol and the fourth group received an implant of 200 mg of $17\beta$-acetoxy-$\Delta^{4,9,11}$-estratriene-3-one. The implants were placed in the subcutaneous tissue situated behind the ear and the animals received the same feed for 90 days. The results are reported in Table I.

TABLE I

|  | Group 1 | Group 2 | Group 3 | Group 4 |
|---|---|---|---|---|
| No. of animals | 39 | 39 | 38 | 39 |
| No. of days fattening | 90 | 85 | 90 | 90 |
| Average weight at time of implantation in Kg. | 441.59 | 442.49 | 439 | 439.61 |
| Average weight at slaughter | 533.05 | 549.85 | 540.60 | 530.65 |
| Weight gain in Kg. | 91.46 | 107.36 | 101.60 | 91.03 |
| Average daily weight gain in Kg. | 1.016 | 1.263 | 1.142 | 1.034 |

The results of Table I show that the average weight gain of the animals of group 2 is clearly superior to that of the other group. The difference between the weight gain of group 2 and the control group is superior to the difference in weight between groups 3 and 4 and the control group. The weight gain of group 2 less than the weight gain of the control group is greater than the weight gain of group 3 less the weight gain of the control group plus the weight gain of group 4 less the weight gain of the control group. This means that the daily average weight gain for the animals of group 2 is clearly superior to that of the other groups.

EXAMPLE 3

The procedure of Example 2 was repeated with male Pie red calves for a period of 28 days after implantation and the results are reported in Table II.

TABLE II

|  | Group 1 | Group 2 | Group 3 | Group 4 |
|---|---|---|---|---|
| No. of animals | 39 | 39 | 38 | 35 |
| Weight gain in Kg. | 33.31 | 42.59 | 37.211 | 35.18 |
| Average daily weight gain in Kg. | 1.190 | 1.521 | 1.330 | 1.256 |

The results of Table II show that the average weight gain of the animals of group 2 is clearly superior to that of the other groups. The difference between the weight gain of group 2 and the control group is superior to the difference in weight between groups 3 and 4 and the control group. The weight gain of group 2 less than the weight gain of the control group is greater than the weight gain of group 3 less the weight gain of the control group plus the weight gain of group 4 less the weight gain of the control group. This means that the daily average weight gain for the animals of group 2 is clearly superior to that of the other groups.

EXAMPLE 4

The test of Example 2 was repeated with male calves of the Normandy strain with the animals divided into a first control group and the second group received composition C of Example 1. 49 days after the implantation, the animals were slaughtered and the results are reported in Table III.

TABLE III

|  | Group 1 | Group 2 |
|---|---|---|
| No. of animals | 12 | 13 |
| No. of days of fattening | 49 | 49 |
| Average weight at start in Kg. | 105.17 | 105.84 |
| Average weight at end of test in Kg. | 180.25 | 189.77 |
| Average weight gain in Kg. | 75.08 | 83.93 |
| Average daily weight gain in Kg. | 1.532 | 1.713 |

The results of Table III clearly show that the treated animals have a much superior weight gain than the controls.

EXAMPLE 5

The test of Example 4 was repeated with female calves of crossed races and the animals were divided into a first control group, a second group which received an implant of composition B and a third group which received an implant of composition C. The results are reported in Table IV.

TABLE IV

|  | Group 1 | Group 2 | Group 3 |
|---|---|---|---|
| No. of animals | 18 | 18 | 18 |
| No. of days of fattening | 77 | 77 | 77 |
| Average weight at start in Kg. | 103.44 | 103.22 | 102.83 |
| Average weight at end of test in Kg. | 198.22 | 209.83 | 218.50 |
| Average weight gain in Kg. | 94.78 | 106.61 | 115.67 |
| Average daily weight gain in Kg. | 1.231 | 1.385 | 1.502 |

The results of Table IV show the weight gain of the animals of group 2 is clearly superior to that of the control animals. The weight gain of the animals of group 3 is clearly superior to the animals of group 2 due to the addition of ($\beta$-ethoxy-$\beta$-ethoxy-ethoxy) acetate of dexamethasone which increase the resorption of the two component composition.

EXAMPLE 6

The test of Example 2 was repeated with male calves of French "Frisonne" Pie black race with the animals divided into a first control group, a second group which received an implant of 36 mg of zeranol and a third group which received an implant of composition B. The results are reported in Table V.

TABLE V

|  | Group 1 | Group 2 | Group 3 |
|---|---|---|---|
| No. of animals | 14 | 14 | 13 |
| No. of days of fattening | 57 | 57 | 57 |
| Average weight at start in Kg. | 91.36 | 91.57 | 90.77 |
| Average weight at end of test in Kg. | 164.86 | 173.43 | 181.08 |
| Average weight gain in Kg. | 73.50 | 81.86 | 90.31 |
| Average daily weight gain in Kg. | 1.289 | 1.436 | 1.584 |

The results of Table V show that the weight gain of the animals of group 3 is clearly superior to that of the animals of group 2 which received only zeranol.

Various modifications of the compositions and method of the invention may be made without departing from the spirit or scope thereof and it should be understood that the invention is to be limited only as defined in the appended claims.

We claim:

1. Novel zootechnical composition for increasing the weight of farm animals comprising a mixture of zeranol and an anabolisant steroid of the formula

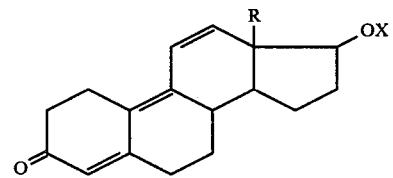

wherein R is alkyl of 1 to 3 carbon atoms and X is selected from the group consisting of hydrogen, lower alkyl of 1 to 6 carbon atoms, lower alkenyl and lower alkynyl of 2 to 6 carbon atoms in which one of the carbon atoms may be replaced with an oxygen atom and acyl of an organic carboxylic acid of 1 to 18 carbon atoms.

2. A composition of claim 1 wherein R is methyl.

3. A composition of claim 1 wherein X is an acyl of an organic carboxylic acid of 1 to 18 carbon atoms.

4. A composition of claim 1 wherein the steroid is 17$\beta$-acetoxy-$\Delta^{4,9,11}$-estratriene-3-one.

5. A composition of claim 1 containing 10 to 100 mg of zeranol and 50 to 400 mg of the said steroid.

6. A composition of claim 1 containing 20 to 60 mg of zeranol and 100 to 300 mg of the said steroid.

7. A composition of claim 1 which further contains a cortisonic steroid to increase the resorption of the composition.

8. A composition of claim 7 wherein the anti-inflammatory agent is ($\beta$-ethoxy-$\beta$-ethoxy-ethoxy) acetate of dexamethasone.

9. A composition of claim 1 in the form of an implant.

10. A method of increasing the weight of farm animals comprising administering to farm animals an amount of a composition of claim 1 sufficient to increase the weight gain of the animals.

11. A method of claim 10 wherein R is methyl.

12. A method of claim 10 wherein X is an acyl of an organic carboxylic acid of 1 to 18 carbon atoms.

13. A method of claim 10 wherein the steroid is 17$\beta$-acetoxy-$\Delta^{4,9,11}$-estratriene-3-one.

14. A method of claim 10 containing 10 to 100 mg of zeranol and 50 to 400 mg of the said steroid.

15. A method of claim 10 containing 20 to 60 mg of zeranol and 100 to 300 mg of the said steroid.

16. A method of claim 10 which further contains a cortisonic steroid to increase the resorption of the composition.

17. A method of claim 10 wherein the anti-inflammatory agent is ($\beta$-ethoxy-$\beta$-ethoxy-ethoxy) acetate of dexamethasone.

18. A method of claim 10 in the form of an implant.

* * * * *